US00PP20975P2

(12) United States Plant Patent
Michalik

(10) Patent No.: US PP20,975 P2
(45) Date of Patent: May 4, 2010

(54) **VARIETY OF *PELARGONIUM* PLANT NAMED 'PACSHIM'**

(50) Latin Name: *Pelargonium peltatum*
Varietal Denomination: Pacshim

(75) Inventor: Andrea Michalik, Dresden (DE)

(73) Assignee: Elsner pac Jungpflanzen, Dresden (DE)

( * ) Notice: Subject to any disclaimer, the term of this patent is extended or adjusted under 35 U.S.C. 154(b) by 0 days.

(21) Appl. No.: 12/316,435

(22) Filed: Dec. 12, 2008

(51) Int. Cl.
*A01H 5/00* (2006.01)

(52) U.S. Cl. ..... Plt./332

(58) Field of Classification Search ..... Plt./332
See application file for complete search history.

*Primary Examiner*—Kent L Bell
(74) *Attorney, Agent, or Firm*—The Webb Law Firm

(57) ABSTRACT

'Pacshim' is a new variety of ivy *pelargonium* having a trailing growth habit, strong vigor, and bi-colored red and white flowers.

1 Drawing Sheet

Botanical classification: *Pelargonium peltatum.*
Varietal denomination: 'Pacshim'.

BACKGROUND OF THE INVENTION

The present invention comprises a new and distinct cultivar of *Pelargonium peltatum* known by the varietal name 'Pacshim'. The new variety was discovered in Dresden, Germany in the Summer of 2005. The new variety is a result of a planned breeding program using the following procedure: a bulk of different genotypes were crossed to obtain big, single flowers with a dark red color; cuttings of the seedling with the best flowering characteristics and best growth habit were grown onto pelargonium variety 'Pactomgimex' (U.S. Plant Pat. No. 13,783) to transfer its bi-colored stripe pattern; when the grafted tips flowered bi-colored, cuttings were made and cloned of the resulting striped new variety, were tested for over two years; and, the most stable clone was selected as the new variety, 'Pacshim'. The purpose of the breeding program was to develop bi-colored, single flowering ivy *pelargoniums* with large flowers. The new variety exhibits a trailing habit, a bi-colored flower type, and all season flowering like 'Pactomgimex'. However, 'Pacshim' has single flowers, while 'Pactomgimex' has semi-double flowers. Further, the new variety is more vigorous and has bigger umbels than 'Pactomgimex'. The new variety was first asexually reproduced by cuttings in the Summer of 2005 in Dresden, Germany. The new variety has been trial and field tested and has been found to retain its distinctive characteristics and remain true to type through successive propagations.

The new variety was grown in a greenhouse in a 12 cm pot in Dresden Germany using four applications of cycocel 720 0.2%. The new variety was pinched twice during development. The new variety has a response time of twelve weeks from a rooted cutting to flowering in a 12 cm container.

The following traits have been repeatedly observed and are determined to be unique characteristics of 'Pacshim'. Characteristics that distinguish 'Pacshim' as a new and distinct cultivar from others known to the breeder include:

1) Strong vigor;
2) Good trailing habit;
3) All season flowering;
4) Stable bi-colored flowers; and
5) Big, single flowers.

DESCRIPTION OF THE DRAWING

The accompanying photographic drawing illustrates the new variety, with the color being as nearly true as is possible with color illustrations of this type.

DESCRIPTION OF THE PLANT

Figure 1:
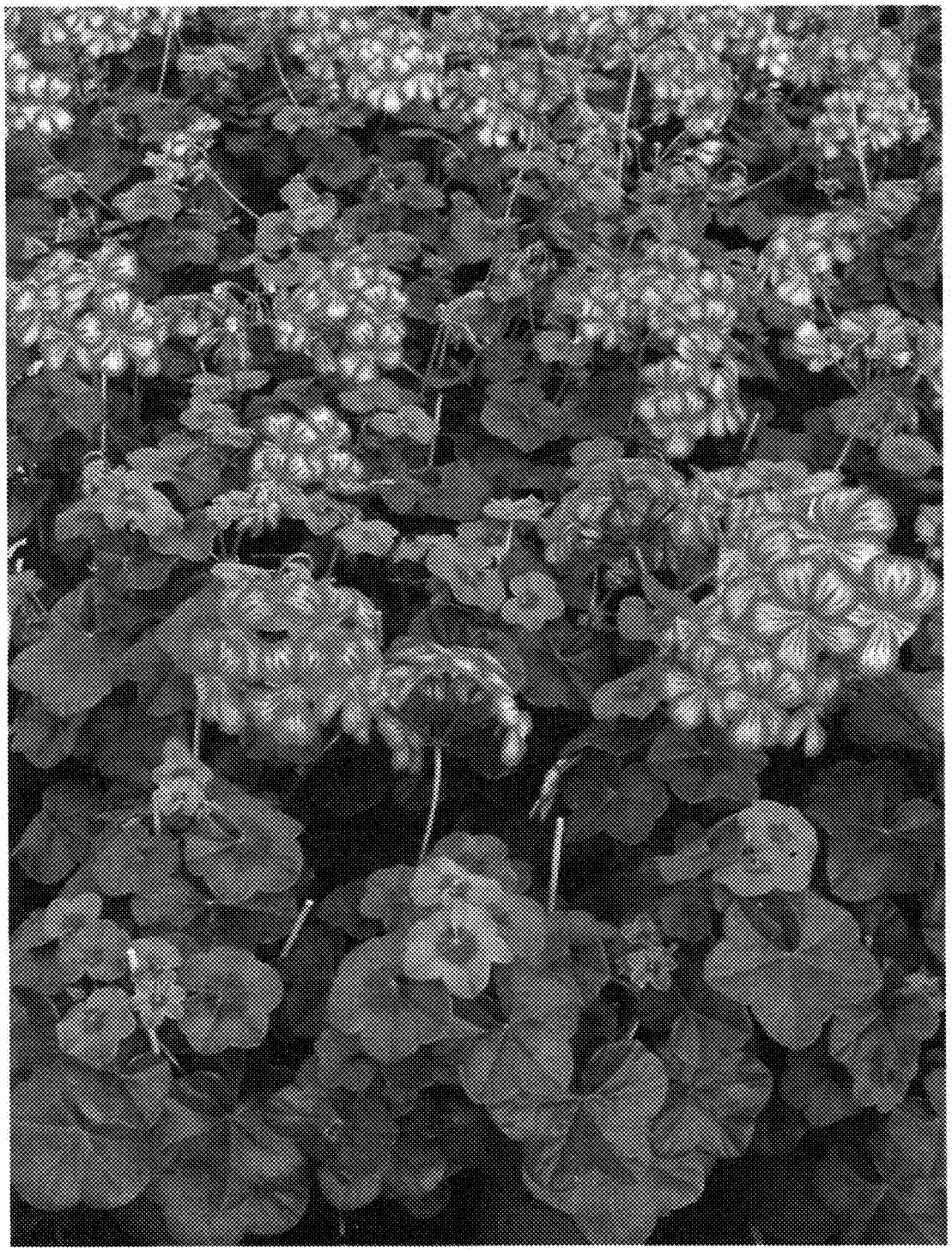

The following detailed description sets forth the characteristics of the new cultivar. The data which defines these characteristics were collected by asexual reproductions carried out in Dresden, Germany. The color readings were taken indoors in room with no direct sunlight and no artificial light. The new variety was six months from a rooted cutting when described. Color references are primarily to the 1995 R.H.S. Colour Chart of The Royal Horticultural Society of London.

PLANT

Market class: Ivy.
Time to initiate roots: About 18 days at about 20–23° C.
Time to develop roots: About 21 days at about 18–20° C.
Rooting habit: Freely branching roots.
Form: Trailing.
Height from media surface to top of foliage: 23 cm.
Height from media surface to top of flowers: 27 cm.
Strength (need for artificial support): Long branches need support during production.
Branching habit: Freely branching.
Plant diameter: 50 cm.
Vigor: Very high.
Stem:
- *Main stem length.*—30–50 cm.
- *Diameter.*—5 mm.
- *Color.*—148A to 178A.
- *Texture.*—Sticky, a little bit rough.
- *Pubescence.*—Medium.
- *Internode length.*—2–7 cm.

Lateral branches:
- *Length.*—Primary: 20–40 cm. Secondary: 2–10 cm.
- *Diameter.*—Primary: 3 mm. Secondary: 3 mm.
- *Internode length.*—2–7 cm.
- *Texture.*—Sticky, a little bit rough.

*Pubescence.*—Medium.
*Color.*—144A to 178A.

Foliage:
*Arrangement.*—Mostly opposite.
*Stipules.*—Size: Length: 10 mm. Width: 5 mm. Color: 146A.
*Zone.*—Location: 2 cm from margin. Color: 200B on young leaves, not present on older leaves.
*Size of leaf.*—Length: 4 cm. Width: 6 cm.
*Shape of leaf* (*generally*).—Ivy shaped.
*Shape of apex.*—Cuneate.
*Shape of base.*—Partially overlapping.
*Texture.*—Rough and leathery.
*Aspect.*—Glossy.
*Margin type.*—Entire.
*Pubescence.*—Upper surface: Light. Lower surface: Very light.
*Color.*—Young leaves: Upper surface: Darker than 146A. Lower surface: 146A. Mature leaves: Upper surface: Darker than 146A. Lower surface: 146A.
*Petiole.*—Length: 2 cm. Diameter: 2 mm. Color: 146A.
*Veins.*—Venation type: Palmate. Color: Upper surface: Not present. Lower surface: 144A.

INFLORESCENCE

Bud:
*Stage of development when bud characteristics determined.*—Before color appears.
*Shape of cluster.*—Bell-shaped.
*Diameter of cluster.*—4 cm.
*Number of buds per cluster.*—6–10.
*Shape of individual bud.*—Spindle-shaped.
*Length of individual bud.*—15 mm.
*Width of individual bud.*—6 mm.

Natural flowering season: Spring until frost in moderate climates.
Blooming habit: Continuous and early blooming.
Umbel diameter.—10–12 cm.
Umbel depth.—6 cm.
Borne: Umbel, flowers on pedicel, pedicel on peduncle.
Inflorescence position: Above foliage.
Number of inflorescences per lateral branch: About 3 at the same time.
Lastingness of an individual flower: 6–10 days.

Florets:
*Form.*—Flat.
*Number per umbel.*—6–10.
*Diameter.*—5 cm.
*Depth.*—2 cm.

Petals:
*Color.*—Upper surface: Margin and stripes 46A, middle areas 49D. Lower surface: Margin and stripes 53C, middle areas 49D.
*Shape.*—Spoon-like.
*Length.*—28 mm.
*Width.*—24 mm.
*Apex shape.*—Round.
*Base shape.*—Pointed.
*Margin.*—Entire.
*Number per floret.*—5.
*Texture.*—Velvety.
*Tonality from a distance.*—Bi-colored red/white.

Petaloids: None present.

Pedicel:
*Length.*—4 cm.
*Diameter.*—15 mm.
*Color.*—144A.

Peduncle:
*Length.*—8–10 cm.
*Diameter.*—3 mm.
*Texture.*—Sticky, a little bit rough.
*Color.*—144A to 178A.

Fragrance: None present.
Disease resistance: None observed to date.
Temperature tolerance: Average.
Drought tolerance: Average.

REPRODUCTIVE ORGANS

Stamens:
*Number* (*per flower*).—7.
*Filament.*—Length: 10 mm. Color: Lower part white, upper part 63B.
*Anthers.*—Shape: An elongated short tube. Length: 2 mm. Color: 200A to 178A.
*Pollen.*—Color: 167A. Amount (generally): Plentiful.

Pistils:
*Number.*—1.
*Length.*—12 mm.
*Style.*—Length: 9 mm. Color: 56D.
*Stigma.*—Shape: Actinomorphic, 5 parted. Color: 59A. Size: Depth: 3 mm. Width: 5 mm.
*Ovaries.*—Pubescence: Present. Length: 5 mm. Width: 2 mm. Color: 138D.

I claim:

1. A new and distinct variety of *pelargonium* plant named 'Pacshim' as is herein described and illustrated.

* * * * *